United States Patent [19]

Ito et al.

[11] Patent Number: 4,999,513
[45] Date of Patent: Mar. 12, 1991

[54] PARTICLE MEASURING APPARATUS

[75] Inventors: Yuji Ito, Chigasaki; Moritoshi Miyamoto, Kawasaki, both of Japan

[73] Assignee: Canon Kabushiki Kaisha, Tokyo, Japan

[21] Appl. No.: 402,358

[22] Filed: Sep. 5, 1989

[30] Foreign Application Priority Data

Sep. 9, 1988 [JP] Japan ................. 63-226001
Sep. 9, 1988 [JP] Japan ................. 63-226002
Nov. 18, 1988 [JP] Japan ................. 63-291566

[51] Int. Cl.$^5$ ..................... G01N 15/06
[52] U.S. Cl. ..................... 250/575; 356/442
[58] Field of Search ............ 250/575, 574, 573; 356/343, 341, 336, 442, 339, 441

[56] References Cited

U.S. PATENT DOCUMENTS

| | | | |
|---|---|---|---|
| 3,680,960 | 8/1972 | Uchino | 250/575 |
| 3,775,013 | 11/1973 | Simms | 356/442 |
| 4,643,566 | 2/1987 | Ohe et al. | 356/72 |
| 4,690,561 | 9/1987 | Ito | 356/339 |
| 4,715,708 | 12/1987 | Ito | 356/72 |
| 4,893,929 | 1/1990 | Miyamoto . | |
| 4,896,961 | 1/1990 | Ito . | |

Primary Examiner—David C. Nelms
Attorney, Agent, or Firm—Fitzpatrick, Cella, Harper & Scinto

[57] ABSTRACT

This specification discloses a particle measuring apparatus characterized by means for passing a particle to be examined to a portion to be examined. First applying means applies an irradiating light from a first direction to the portion to be examined, second applying means applies an irradiating light from a second direction differing from the first direction to the portion to be examined. First and second photometering means photomets the lights radiated from the portion to be examined by the application of lights to the particle to be examined, relative to the first and second applying means, respectively.

42 Claims, 6 Drawing Sheets

PARTICLE MEASURING APPARATUS

BACKGROUND OF THE INVENTION

1. Field of the Invention

This invention relates to a particle measuring apparatus for effecting measurement of particles to be examined by applying a light to the particles to be examined and photometering light such as transmitted light or scattered light or fluorescence radiated from the particles to be examined.

2. Related Background Art

In the conventional particle measuring apparatus, for example, a flow cytometer, a light has been applied from a predetermined direction to particles to be examined such as cells flowing one by one at a high speed, and light radiated thereby from the particles to be examined, i.e., transmitted light or scattered light or fluorescence has been photometered, whereby the information regarding the diameters and natures of the particles to be examined has been obtained and the particles to be examined have been statistically analyzed from this information regarding a number of cells.

In this conventional flow cytometer, the shape and size of the light beam applied to the particles to be examined are set such that the size in the direction of flow is substantially equal to or somewhat larger than the particle to be examined and the size in a direction orthogonal to the direction of flow is larger than the particle to be examined, whereby light application can be accomplished with a uniform intensity even if there occurs deviation to the flow position of the particle to be examined. Besides this, use has also been made of the slit scan system in which a slit-shaped beam having its beam size in the direction of flow made thinner than the size of the particle to be examined is applied to thereby detect more detailed information of the particle to be examined. Recently, it has also been used to mix latex particles sensitized by an antibody with a sample material, cause the aggregation of the latex particles by antigen/antibody reaction, and detect the size of this latex aggregation by the use of a flow cytometer, thereby discriminating particular antigen in the sample material.

Also, it has generally been practised to effect analysis by the image information of particles to be examined by the use of an apparatus such as an optical microscope or an electronic microscope, apart from a flow cytometer. Particularly recently, use has also been made of an apparatus in which a cell is two-dimensionally scanned by a minute laser spot to thereby obtain a high-contrast image which is reflective of the internal structure of a cell.

In these conventional apparatuses, however, only the information of each particle to be examined as seen in one direction could be taken out and three-dimensional grasp of the particles to be examined could not be accomplished.

Also, U.S. Pat. No. 3,826,364 discloses an apparatus of a construction in which two laser sources of different wavelengths are prepared and one laser light is applied to a first portion to be examined to produce forward scattered light and the other laser light is applied to a second portion to be examined differing from the first portion to be examined to excite fluorescence. In this apparatus, however, two kinds of parameters are measured not at the same position but at different positions and therefore, when particles to be examined move from the first portion to be examined to the second portion to be examined, rotation, drift or the like occurs and the particles to be examined which are in the same state cannot always be measured from different directions.

SUMMARY OF THE INVENTION

An object of the present invention is the provision of a particle measuring apparatus which can obtain information from a plurality of directions regarding each particle to be examined and can accomplish analysis of high accuracy.

A further object of the present invention is the provision of a particle measuring apparatus which obtains bits of information from a plurality of directions regarding each particle to be examined and compares them to thereby discriminate the degree of sphericity of the particle to be examined.

Still a further object of the present invention is the provision of a particle measuring apparatus in which lights of different wavelengths are applied from a plurality of direction to a particle to be examined and lights radiated from the particle to be examined are photometered for each wavelength, whereby bits of information from the plurality of directions can be obtained.

Yet still a further object of the present invention is the provision of a particle measuring apparatus in which light application is effected alternately from a plurality of directions to a particle to be examined within a short time and lights radiated from the particle to be examined are photometered, whereby bits of information from the plurality of directions can be obtained.

DESCRIPTION OF THE PREFERRED EMBODIMENTS

Some embodiments of the particle measuring apparatus of the present invention will hereinafter be described in detail with reference to the drawings.

Figure 1:
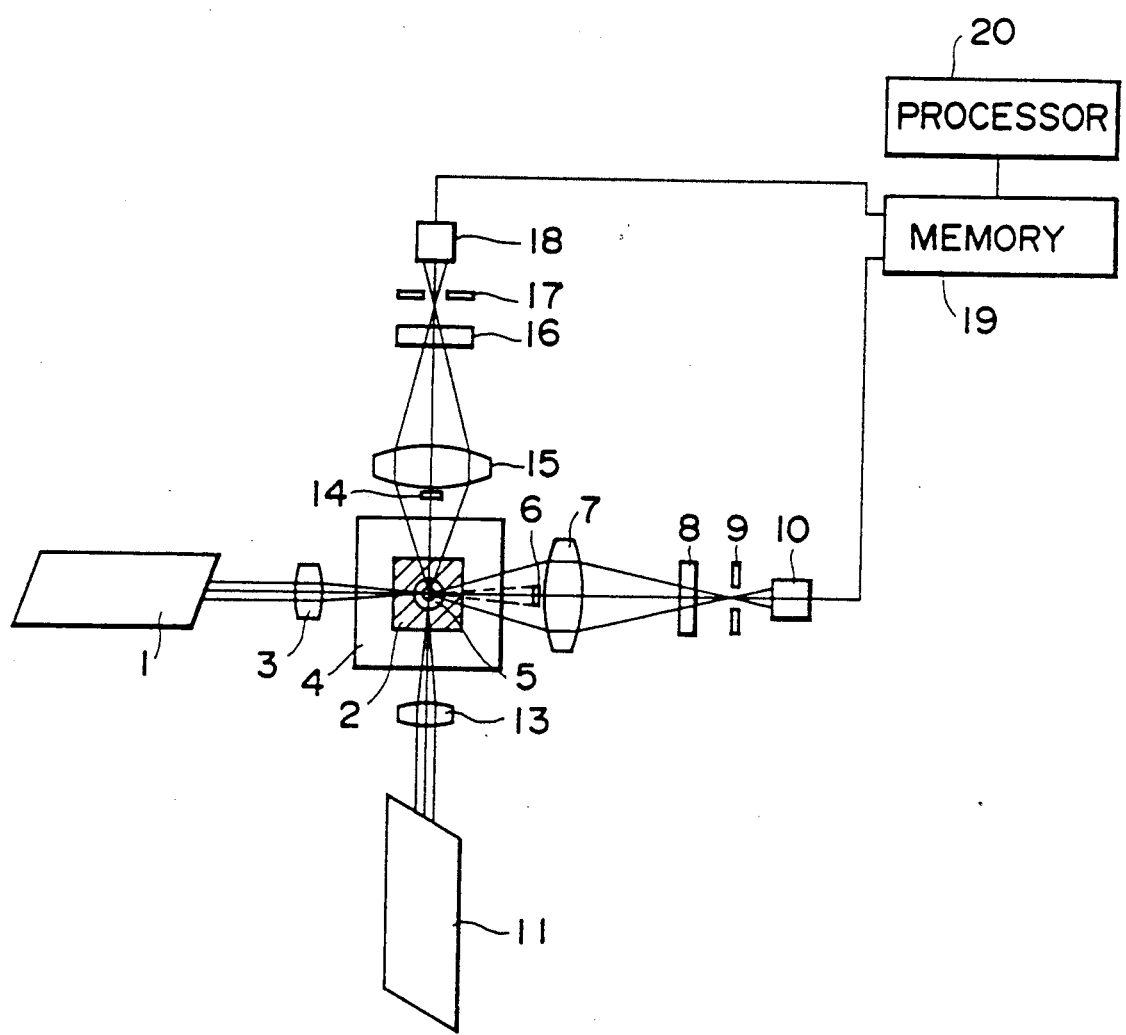
FIG. 1 shows the construction of an embodiment of the present invention.
Figure 2:
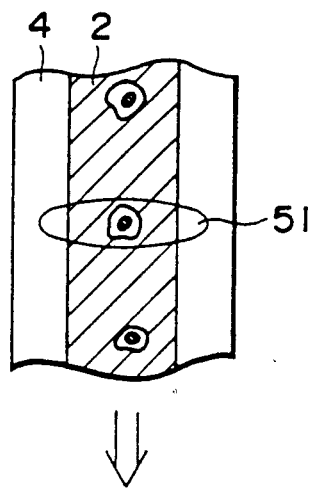
FIG. 2 is a side view of a flow cell showing an example of the shape of a beam spot.
Figure 3:
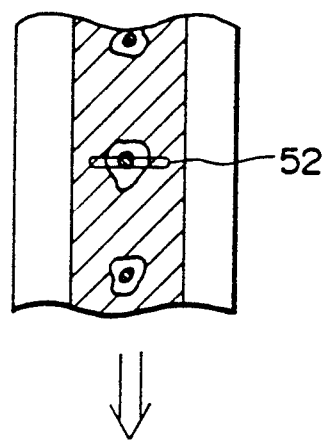
FIG. 3 shows a modification of the shape of the beam spot.

Referring to FIG. 1 which shows the construction of an embodiment of the present invention, the reference numeral 1 designates a laser source which emits a laser light, and the reference numeral 3 denotes an imaging optical system comprising a cylindrical lens or the like. The laser source 1 and the imaging optical system 3 together form first light applying means. The laser light of wavelength $\lambda_1$ emitted from the laser source 1 is imaged on a through-flow portion 2 in a flow cell 4 of transparent glass by the imaging optical system 3. The shape of the beam spot imaged on a portion to be examined by the imaging optical system 3 at this time is an elliptical shape laterally long relative to the flow of particles to be examined, as indicated by 51 in FIG. 2. This is for enabling the light to be applied to the particles to be examined with a substantially uniform intensity even if the flow position of the particles to be examined in the portion to be examined somewhat deviates from the central position in the through-flow portion 2. Alternatively, the shape of said beam spot may be a slit-like shape which is very short in the longitudinal direction as shown in FIG. 3 and slit scan measurement may be effected. By this method, the information of the various portions of the particle to be examined can be time-serially measured and more detailed information of the particle to be examined can be obtained.

Also, a laser light of wavelength $\lambda_2$ differing from the aforementioned wavelength $\lambda_1$ is emitted from a laser source 11 as second light applying means. This laser light, like the laser light from the first light applying means, is imaged on the portion to be examined in the flow cell from a direction orthogonal to the first light applying means by an imaging lens system 13.

The particles to be examined such as blood corpuscle cells or latex aggregations are caused to flow to the through-flow portion 2 in the flow cell 4 one particle by one or one lump by one in a direction perpendicular to the plane of the drawing sheet by the laminar sheath flow principle which is popular in this field, and successively pass through the portion to be examined in the flow cell 4 on which the laser light of wavelength $\lambda_1$ and the laser light of wavelength $\lambda_2$ are imaged at a time. When there is no particle 5 to be examined in the portion to be examined, the laser light from the laser source 1 rectilinearly travels through the flow cell 4 and is intercepted by a stopper 6 and likewise, the laser light from the laser source 11 is intercepted by a stopper 14. However, when the particle to be examined comes to the portion to be examined and the laser lights are applied to the particle to be examined, light scattering is caused by the particle to be examined and there are produced scattered lights of wavelengths $\lambda_1$ and $\lambda_2$. Condensing lenses 7 and 15 are disposed in the straight optical paths of the laser sources 1 and 11, respectively, and scattered lights of predetermined angles are condensed thereby. Here, as regards the scattered light condensed by the lens 7, only the light of wavelength $\lambda_1$ is selectively transmitted through a barrier filter 8. That is, only the scattered light produced from the light applied by the first light applying means is selected. The light of wavelength $\lambda_1$ transmitted through the barrier filter 8 passes through a stop 9 and the intensity thereof is detected by a photodetector 10.

As regards the scattered light condensed by the lens 15, only the light of wavelength $\lambda_2$ is selected by a barrier filter 16. That is, only the scattered light by the second light applying means is selected and the intensity of the light of wavelength $\lambda_2$ is detected by a stop 17 and a photodetector 18. The outputs of the photodetectors 10 and 18 are connected to memory means 19, and the respective detected data are memorized discretely from each other. Thus, measurement data from different angles are obtained about a particle to be examined, and the calculation of the particle measurement is effected by processor means 20 on the basis of the contents of the memory means 19.

A calculation method for discriminating the shape of the particle to be examined from the detected data will now be described as an example of the method of using the above-described apparatus.

Figure 9A:
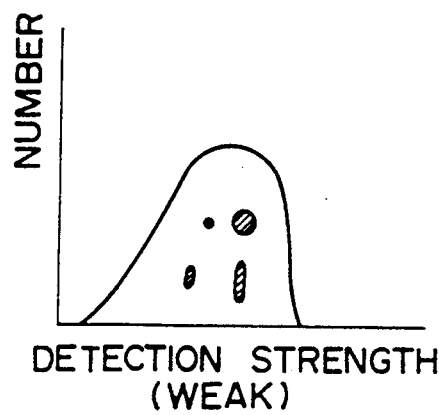
FIGS. 9A and 9B are histograms of scattered light measurement data.
Figure 9B:
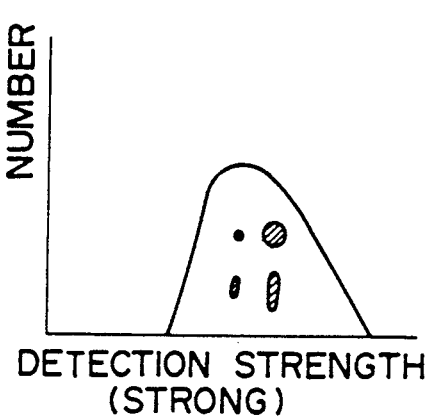
Figure 10A:
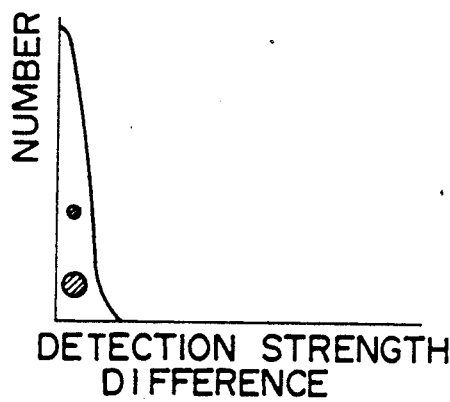
FIGS. 10A and 10B are histograms representing the asphericity of particles to be examined.
Figure 10B:
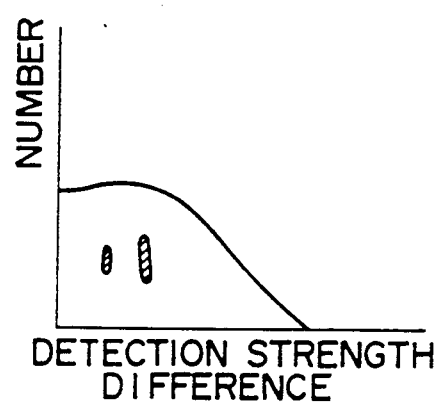

First and second memory portions are provided in the memory means 19, and of the two scattered light detected data obtained from a particle to be examined, the greater data is memorized in the first memory portion, and the smaller data is memorized in the second memory portion. When the two data are of the same value, the same value is memorized in the first and second memory portions. The respective data memorized in the first and second memory portions are shown as histograms in FIGS. 9A and 9B. In FIG. 9, the horizontal axis represents the detected intensity of the scattered light, and the vertical axis represents the number of particles to be examined. Generally it is known that the larger is the particle to be examined, the greater is the detected intensity of the scattered light. Here, if the particle to be examined is perfectly spherical, the sizes of the particle to be examined as it is seen from two directions are the same and the two detected data obtained are substantially of the same value. On the other hand, if the particle to be examined is aspherical, the size thereof differs depending on the direction in which the particle to be examined is seen. Consequently, the measured value of the scattered light also differs and the values memorized in the first and second memory portions become different. The more aspherical is the particle to be examined, the greater is the degree of difference. That is, the degree of difference between the data memorized in the first and second memory portions represents the asphericity of the particle to be examined. The degree of difference may be represented by the difference between the two data or by the ratio therebetween. FIGS. 10A and 10B are histograms of the difference taken between the data in the first and second memory portions, and FIG. 10A shows the result when the particle to be examined is perfectly spherical, and FIG. 10B shows the result when the particle to be examined is aspherical. In FIG. 10, the horizontal axis represents the difference between the data in the first and second memory portions, i.e., the asphericity of the particle to be examined, and the vertical axis represents the number of particles to be examined. The horizontal axis may use the ratio instead of the difference. As is apparent from this, as regards a spherical particle to be examined, data concentrates in the vicinity of the left end on the histogram as shown in FIG. 10A, whereas an aspherical particle to be examined exhibits the tendency that the data widens greatly as shown in FIG. 10B. Thus, from the patterns of the histograms, the spherical shape and the aspherical shape can be distinguished from each other and further, the degree of aspherical shape can be discriminated. In the present embodiment, the discrimination between the patterns of the histograms is automatically effected by the discrimination circuit of the processor means 20 by the use of the pattern recognizing technique, but alternatively, a person may judge by seeing what is displayed.

Figure 11A:
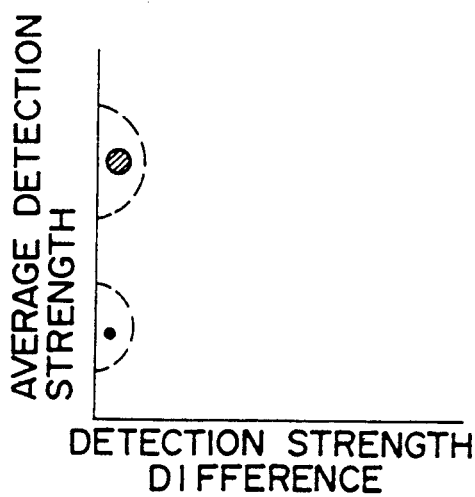
FIGS. 11A and 11B are cytograms representing the shapes of particles to be examined.
Figure 11B:
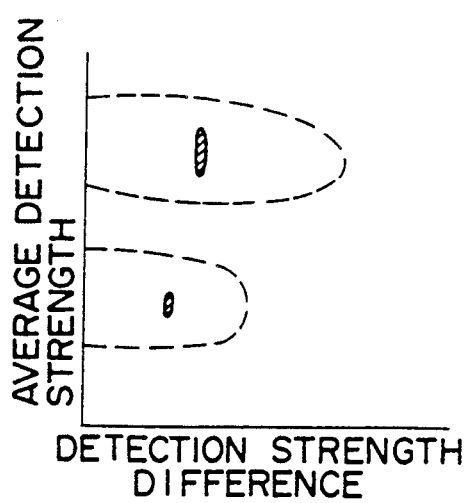

However, from these histograms, the asphericity of the particle to be examined can be judged, but the size of the particle to be examined cannot be judged at the same time. So, use is made of cytograms as shown in FIGS. 11A and 11B. In FIG. 11, the horizontal axis represents the difference between the intensities of the scattered lights, i.e., the difference between the data in the first and second memory portions, in other words, the asphericity of the particle to be examined. In contrast, the vertical axis represents the average value of the intensities of the two scattered lights, i.e., the average value of the data in the first and second memory portions, that is, the rough particle diameter. The data of a number of particles to be examined are plotted by one point by one on the cytogram, and the tendency of plot aggregation differs depending on the shapes of the particle to be examined. For example, in FIG. 11A, particles to be examined which are perfectly spherical and differ in size are distinguished from each other. Two kinds of particles to be examined differing in size are plotted substantially within ranges encircled by dotted lines, respectively. Also, FIG. 11B shows a cytogram in which the range of plot in conformity with the degree of asphericity of the particles to be examined widens laterally and is separated in the vertical direction by the sizes of the particles to be examined. By the representation in such a cytogram, the shape (asphericity and size) of the particles to be examined can be discriminated depending on in what distribution it is displayed on the cytogram. Further, even in a case where particles to be examined having a plurality of kinds of shapes are mixedly present in a sample being measured, distinction between and counting of the shapes can be accomplished. The judgment of the cytogram pattern, as previously described, may be automatically done by the pattern recognition or by a person.

As described above, the shapes of the particles to be examined can be discriminated and counted to thereby accomplish various analyses of the particles, such as, for example, discrimination between and counting of the kinds of blood corpuscles, discrimination between and counting of the kinds of microorganisms, and detection of the antigen/antibody reaction using sensitizing latex. Further, by photometering the scattered lights from two directions as well as fluorescence radiated from a fluorescence-dyed particle to be examined, and adding the biochemical natures or the like of the particle to be examined obtained from the intensity of the fluorescence as the parameters of particle analysis, it is possible to accomplish more detailed analysis. Furthermore, transmitted light can be used instead of scattered light although accuracy is somewhat reduced.

[Embodiment 2]

Figure 4:
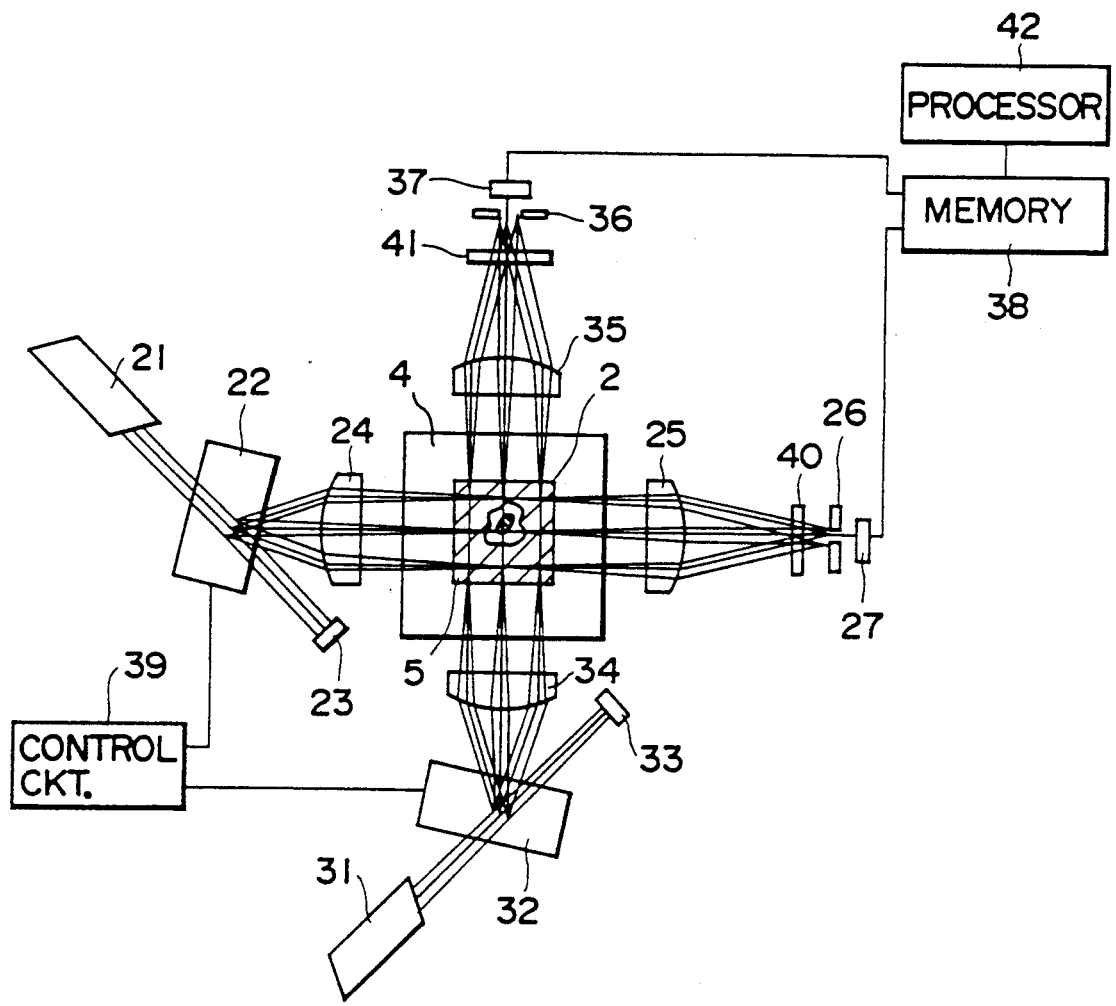
FIG. 4 shows the construction of a second embodiment of the present invention.
Figure 5:
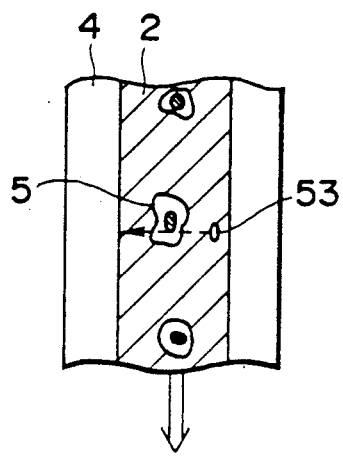
FIG. 5 is a side view of a flow cell showing an example of the shape of a beam spot.

Description will now be made of an embodiment in which particles to be examined are light-scanned from a plurality of directions to thereby obtain more detailed information of the particles. FIG. 4 shows the construction of such embodiment, and FIG. 5 is a side view of a flow cell portion as seen from the direction in which a laser beam is applied. In FIG. 4, reference numerals identical to those in FIG. 1 designate identical members.

Laser light emitted from a laser source 21 emitting a laser light of wavelength $\lambda_1$ as first light applying means for applying a light to particles to be examined is deflected and scanned at a high speed in a plane intersecting the flow of the particles to be examined by a light deflector (AOD) 22 provided in the optical path. A stopper 23 is provided in the direction of rectilinear travel from the laser source 21 and O-orderlight is cut thereby. The laser light deflected by the light deflector 22 is telecentrically imaged on the portion to be examined of the through-flow portion 2 in the flow cell 4 by an objective lens 24. Here, the size of the imaged spot is smaller than the size of the particles to be examined, as indicated at 53 in FIG. 5.

Also, as second light applying means, a laser source 31 emitting a laser light of wavelength $\lambda_2$ differing from the wavelength $\lambda_1$ of the laser source 21, a light deflector 32, an objective lens 34 and a stopper 33 are disposed in the same manner as the first light applying means, and the portion to be examined is scanned from a direction orthogonal to the first light applying means. Here, the light deflectors 22 and 32 are controlled by a control circuit 39 so as to deflect and scan the lights at the same speed.

Particles 5 to be examined such as the cells of an organism are caused to flow one by one to the through-flow portion 2 by the laminar sheath flow principle. At this time, the scanning speed of the laser spot is set to sufficiently greater than the speed of the flow of the particles to be examined. When as shown in FIG. 4, a particle to be examined comes to the portion to be examined scanned at a high speed by the laser spot 50, the applied beams enter the particle to be examined from the same direction at any scan position because the laser scanning optical system is telecentric, and thus uniform scanning can be accomplished. The laser light of wavelength $\lambda_1$ is scanned on the particle 5 to be examined by the first light applying means, and the light transmitted through the particle to be examined and the light scattered by the particle 5 to be examined are condensed by condensing lenses 25 provided at opposed positions with the flow cell 4 interposed therebetween. The condensed lights are wavelength-selected by a filter 40 passing only the light of wavelength $\lambda_1$ therethrough, and only the transmitted light is selected by a stop 26 disposed at a position conjugate with the light deflector 22, and the intensity of the transmitted light of wavelength $\lambda_1$ is detected by a photodetector 27. Where it is desired to detect not the transmitted light but the scattered light by the particle to be examined, a stopper of the same area as the opening in the stop 26 can be provided instead of the stop 26 to thereby cut the transmitted light and detect the scattered light.

On the other hand, a condensing lens 35 is disposed at a position opposed to the second light applying means with the flow cell 4 interposed therebetween, and the transmitted light and the scattered light from the portion to be examined are condensed thereby and are wavelength-selected by a filter 41 passing only the light of wavelength $\lambda_2$ therethrough, and the intensity of the transmitted light of wavelength $\lambda_2$ is detected by a stop 36 and a photodetector 37. Where it is desired to detect the scattered light, the same means as what has been described above may be adopted.

The outputs of the photodetectors 27 and 37 are connected to a memory unit 38 and are time-serially stored in the memory discretely from each other.

As described above, when a particle to be examined passes through the portion to be examined in which laser lights are scanned from a plurality of different directions at a high speed at a time, the particle to be examined is canned a plurality of times from the respective directions when it passes through the portion to be examined because the scanning speed is set to sufficiently great relative to the passage speed of the particle, and thus substantially two-dimensional scanning is effected on the particle to be examined from a plurality of directions.

Thus, each time a particle to be examined passes through the portion to be examined, data representative of the shape, etc. of the particle to be examined as it is seen from a plurality of directions are stored in the memory unit 38 with respect to each particle to be examined. Particle analysis is effected by subjecting these data to image processing or by the use of the statistic processing such as histogram or cytogram as in the previous embodiment. These calculations are effected by a processor circuit 42.

[Embodiment 3]

A third embodiment of the present invention will now be described, but the construction of the apparatus of the present embodiment is substantially similar to that of the second embodiment and therefore, the present embodiment will hereinafter be described with reference to FIG. 4. While in the previous embodiment, lights from laser sources of different wavelengths are applied to the portion to be examined at a time from different directions and the wavelengths are separated and photometered to thereby obtain bits of information of plural components discretely from each other, the present embodiment is characterized in that lights are alternately applied from a plurality of directions within a short time to thereby measure bits of information of plural components discretely from each other. Here, the switching of the light application is at a very high speed as compared with the flow speed of particles and thus, even if the light application is alternately switched, particles to be examined substantially in the same state are measured from different directions.

The laser sources 21 and 31 may be light sources of different wavelength as in the previous embodiment, or may be laser sources of the same kind. The filters 40 and 41 may be absent. The light defectors 22 and 32 are controlled by the control circuit 15 so that when one of them is scanning the portion to be examined, the other becomes blanking. That is, the particle to be examined is not laser-irradiated from a plurality of directions at a time, but at a certain time, only the laser light from one of the laser sources is applied.

Figure 6:
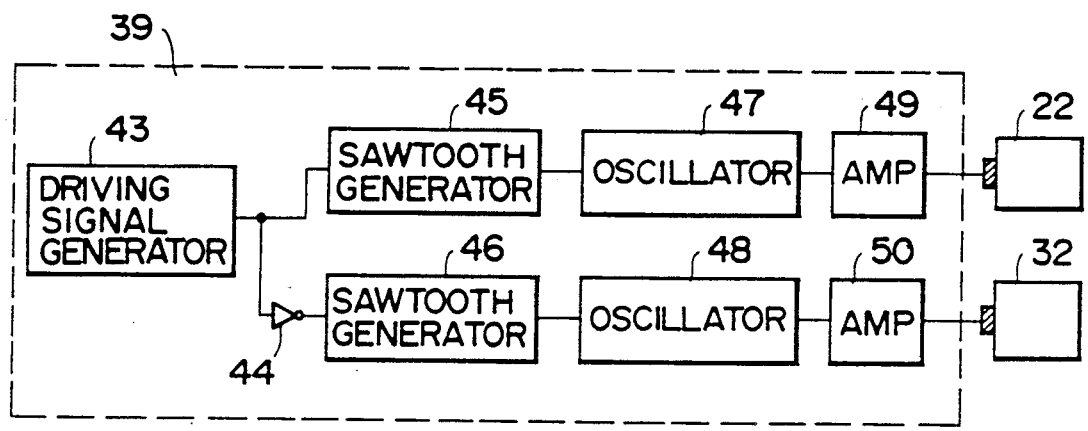
FIG. 6 diagramatically shows a driving circuit for a light deflector.
Figure 7:
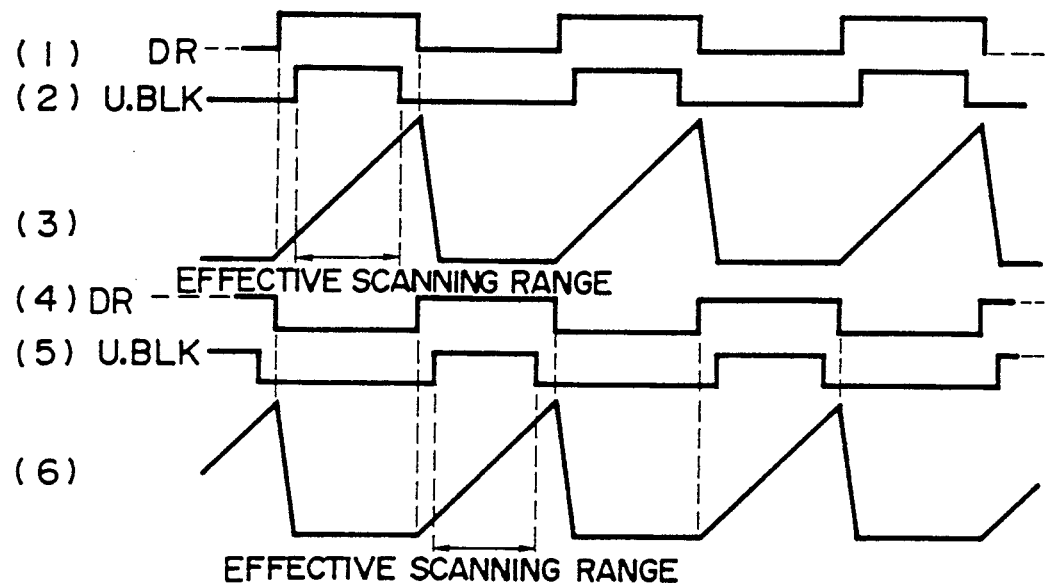
FIG. 7 is a driving timing chart of the light deflector.

FIGS. 6 and 7 illustrate a driving method for the light deflectors 22 and 32 in the control circuit 39. A driving signal generator 43 generates a rectangular wave of 50% duty as shown in FIG. 7(1). This signal is divided into two, one of which is input to a sawtooth generator 45 and the other has its wave form inverted by an inverter 44 as shown in FIG. 7(4) and is input to a sawtooth generator 46. Actually, the U.BLK signals of FIGS. 7(2) and 7(5) determine the effective scanning range. Signals of sawtooth-like wave form as shown in FIGS. 7(3) and 7(6) are obtained by these sawtooth generators 45 and 46, respectively, and these signals provide driving signals for the light deflectors via voltage control type oscillators 47 and 48 and amplifiers 49 and 50, and in the light deflectors 22 and 32, they drive transducers and deflect and scan the lights. Thus, when one is scanning the effective scanning range, the other becomes blanking, and bits of information of the particle as it is seen from respective directions can be taken out separately from each other.

In the above-described second and third embodiments, light deflectors are used to scan light beams, but if use is made of laser sources having the light deflecting function in themselves, the light deflectors will become unnecessary and the construction of the apparatus will become simpler.

[Embodiment 4]

Figure 8:
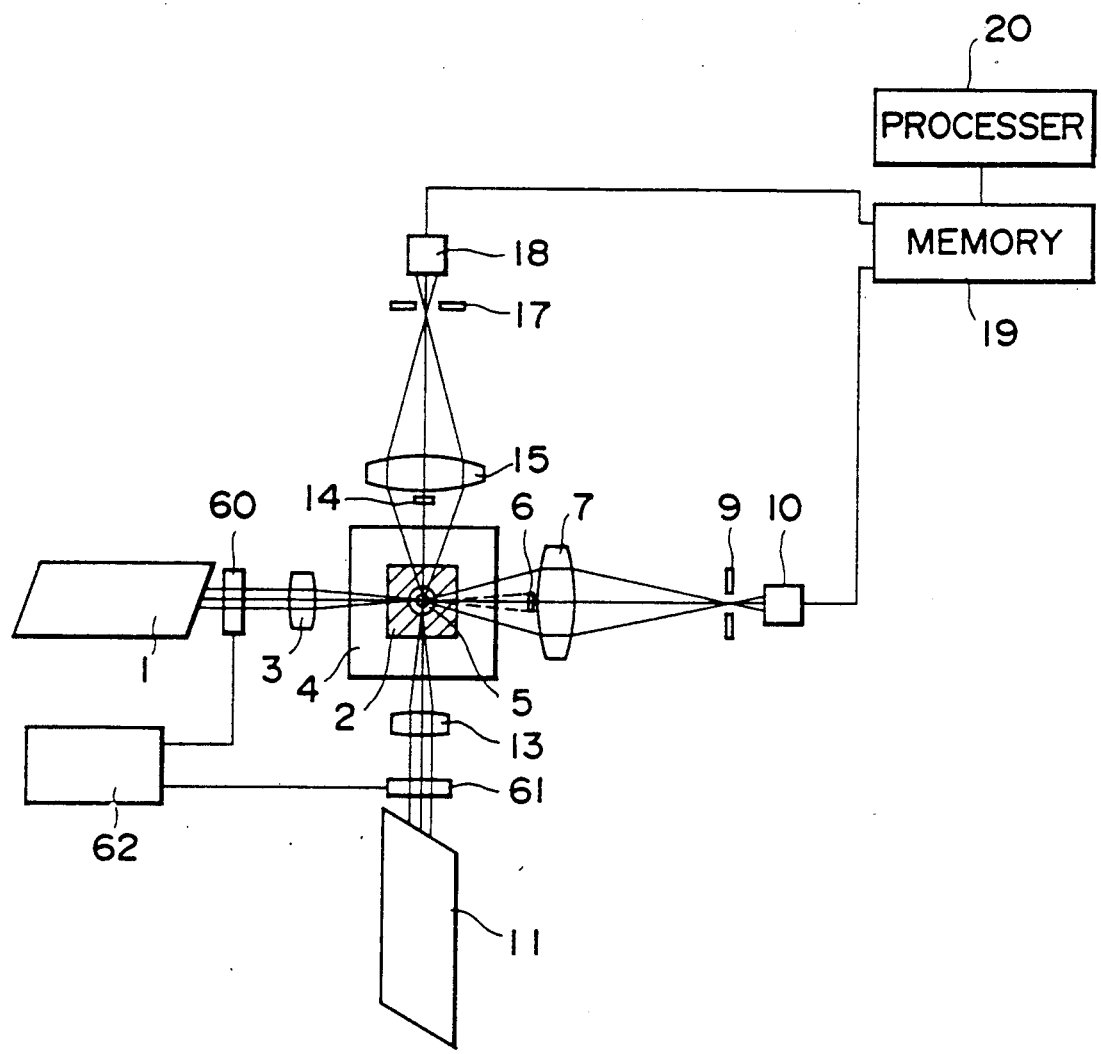
FIG. 8 shows the construction of a fourth embodiment of the present invention.

A fourth embodiment of the present invention will now be described. FIG. 8 shows the construction of this embodiment, but this embodiment is similar to the embodiment of FIG. 1 and therefore, portions common to those two embodiments need not be described in detail.

In FIG. 8, first light limiting means 60 such as a mechanical shutter, a liquid crystal shutter or a chopper is disposed forwardly of the laser source 1, and transmits or intercepts the laser beam by ON-OFF control. Similar second light limiting means 61 is disposed forwardly of the laser source 11. The respective light limiting means 60 and 61 are ON-OFF-controlled by a control circuit 62. The shape of the beam applied to the portion to be examined of the through-flow-portion 6 in the flow cell 7, as in the first embodiment, is the shape as shown in FIG. 2 or 3.

Here, as regards the laser light application by the first and second light applying means, the light limiting means 60 and 61 are controlled by the control circuit 62 and the laser lights are alternately applied within a short time. Consequently, by the passage of the particle to be examined to the portion to be examined, the particle to be examined is alternately light-irradiated from two directions.

The lights thus alternately applied to the particle to be examined and transmitted through and scattered by the particle to be examined or fluorescence radiated from the particle is received by a condensing lens 40 and a photodetector 41 with regard to the first light applying means and is received by a condensing lens 42 and a photodetector 43 with regard to the second light applying means. Which of the transmitted light and the scattered light is detected can be selected by placing a stop or a stopper forwardly of the photodetectors 41 and 43 as in the previous embodiment.

Of the above-described embodiments, in the embodiment wherein lights are alternately applied to the portion to be examined, the forward scattered light or the transmitted light is detected by the photo-detector means disposed in the forward portion of the optic axis of the applied laser light, but it is also possible to use the other photodetector means for the detection of the sideways scattered light and detect the forward scattered light or the transmitted light by one photodetector means and at the same time, detect the sideways scattered light by the other photodetector means.

By effecting the blanking control so that the applied lights from two directions are not applied to the particle to be examined at a time, mixing of the noise by the other applied light is prevented, but if the detection of only the transmitted light or the forward scattered light is aimed at, measurement accuracy will not so much affected even if the applied lights from two directions are applied at a time without the blanking control being effected. This is because the intensity of the sideways scattered light or fluorescence by the application of the second laser light is very weak relative to the intensity of the transmitted light or the forward scattered light by the application of the first laser light which enters the same photodetector means.

Of course, the other photodetector means may not be used also to detect the sideways scattered light, but a detecting optical system for excluse use may be provided. Further, it is also possible to provide a detecting system comprising a dichroic mirror and a barrier filter forwardly of the photodetector in the optical path to thereby detect fluorescence radiated from the particle to be examined. Thereby the measurement parameters can be increased, and this leads to improved measurement accuracy.

The directions in which the laser lights are applied to the portion to be examined are not restricted to those in the embodiments, but the present invention is effective if there is an angle between the directions of application of the first light applying means and the second light applying means.

Also, in the above-described embodiments, lights are applied from two directions to the particle to be examined and bits of information of the particle as it is seen from the two directions are obtained, whereas this is not restrictive, but it is also possible to apply lights from three or more directions to thereby obtain more detailed information.

We claim:

1. A particle measuring apparatus including:
   means for passing individual particles to be examined one by one to a portion to be examined;
   first applying means for applying an irradiating light from a first direction to said portion to be examined;
   second applying means for applying an irradiating light from a second direction differing from said first direction to said portion to be examined;
   first and second photometering means for photometering the lights radiated from said portion to be examined by the application of lights to the individual particle to be examined, relative to said first and second applying means, respectively; and
   means for measuring the individual particles on the basis of the outputs of said first and second photometering means.

2. A particle measuring apparatus according to claim 1, further including control means for controlling so that when one of said first and second applying means is applying a light to the portion to be examined, the other applying means does not apply a light to the portion to be examined.

3. A particle measuring apparatus according to claim 1, wherein said portion to be examined is provided in a flow cell.

4. A particle measuring apparatus according to claim 3, wherein said individual particle is made to flow by a laminar sheath flow principle.

5. A particle measuring apparatus according to claim 1, wherein said particles to be examined are cells.

6. A particle measuring apparatus according to claim 1, wherein said particles to be examined are immunity latex particles.

7. A particle measuring apparatus according to claim 1, wherein said applying means includes a laser light source.

8. A particle measuring apparatus according to claim 1, wherein said first and second photometering means comprise a plurality of detectors for detecting scattered light from said particles to be examined.

9. A particle measuring apparatus according to claim 8, wherein at least one of said first and second photometering means includes a plurality of detectors capable of simultaneously detecting different kinds of light.

10. A particle measuring apparatus including:
    means for passing a particle to be examined to a portion to be examined;
    first applying means for applying an irradiating light from a first direction to said portion to be examined;
    second applying means for applying an irradiating light from a second direction differing from said first direction to said portion to be examined; and
    first and second photometering means for photometering the lights radiated from said portion to be examined by the application of lights to the particle to be examined, relative to said first and second applying means, respectively,
    wherein said applying means deflect the irradiating lights by light deflecting means and light-scan the portion to be examined in a direction intersecting the direction of passage of the particle to be examined.

11. A particle measuring apparatus including:
    means for passing a particle to be examined to a portion to be examined;
    first applying means for applying a light of a first wavelength from a first direction to said portion to be examined;
    second applying means for applying a light of a second wavelength from a second direction differing from said first direction to said portion to be examined; and
    first and second photometering means for photometering the lights of said first and second wavelengths, respectively, radiated from said portion to be examined by the application of lights to the particle to be examined.

12. A particle measuring apparatus according to claim 11, wherein the lights are applied to the portion to be examined at a time by said first and second applying means, and said first and second photometering means separate said first wavelength and said second wavelength and photometer said lights.

13. A particle measuring apparatus according to claim 11, wherein said applying means deflect the irradiating lights by light deflecting means and light-scan the portion to be examined in a direction intersecting the direction of passage of the particle to be examined.

14. A particle measuring apparatus according to claim 11, wherein said portion to be examined is provided in a flow cell.

15. A particle measuring apparatus according to claim 14, wherein said individual particle is made to flow by a laminar sheath flow principle.

16. A particle measuring apparatus according to claim 11, wherein said particles to be examined are cells.

17. A particle measuring apparatus according to claim 11, wherein said particles to be examined are immunity latex particles.

18. A particle measuring apparatus according to claim 11, wherein said applying means includes a laser light source.

19. A particle measuring apparatus according to claim 11, wherein said first and second photometering means comprises a plurality of detectors for detecting scattered light from said particles to be examined.

20. A particle measuring apparatus according to claim 19, wherein at least one of said first and second photometering means includes a plurality of detectors capable of simultaneously detecting different kinds of light.

21. A particle measuring apparatus including:
    means for passing a particle to be examined to a portion to be examined;

first applying means for applying an irradiating light from a first direction to said portion to be examined;

second applying means for applying an irradiating light from a second direction differing from said first direction to said portion to be examined;

first and second photometering means for photometering the lights radiated from said portion to be examined by the application of lights to the particle to be examined, relative to said first and second applying means, respectively;

comparing means for comparing the output values of said first and second photometering means; and discriminating means for discriminating the shape of the particle to be examined from the result of the comparison by said comparing means.

22. A particle measuring apparatus according to claim 21, wherein said comparing means calculates the difference or ratio between the output values of said first and second photometering means.

23. A particle measuring apparatus according to claim 22, wherein by the use of a number of comparison data obtained by said comparing means, statistic processing is effected by said discriminating means to thereby discriminate the shape of the particle to be examined.

24. A particle measuring apparatus according to claim 23, wherein said statistic processing discriminates the degree of sphericity of the particle to be examined by the distributed state of data on a histogram or a cytogram.

25. A particle measuring apparatus according to claim 21, further including control means for controlling so that when one of said first and second applying means is applying a light to the portion to be examined, the other applying means does not apply a light to the portion to be examined.

26. A particle measuring apparatus according to claim 21, wherein said first and second applying means apply lights of different wavelengths and effect the application of said lights to the portion to be examined at a time.

27. A particle measuring apparatus according to claim 21, wherein said applying means deflect the irradiating lights by light deflecting means and light-scan the portion to be examined in a direction orthogonal to the direction of passage of the particle to be examined.

28. A particle measuring apparatus according to claim 21, wherein said portion to be examined is provided in a flow cell.

29. A particle measuring apparatus according to claim 28, wherein said individual particle is made to flow by a laminar sheath flow principle.

30. A particle measuring apparatus according to claim 21, wherein said particles to be examined are cells.

31. A particle measuring apparatus according to claim 21, wherein said particles to be examined are immunity latex particles.

32. A particle measuring apparatus according to claim 21, wherein said applying means includes a laser light source.

33. A particle measuring apparatus according to claim 21, wherein said first and second photometering means comprises a plurality of detectors for detecting scattered light from said particles to be examined.

34. A particle measuring apparatus according to claim 33, wherein at least one of said first and second photometering means includes a plurality of detectors capable of simultaneously detecting different kinds of light.

35. A particle measuring apparatus, comprising:

means for passing particles to be examined one by one to a portion to be examined;

first detection means for detecting two-dimensional information of the particle at the portion to be examined from a first direction;

second detection means for detecting two-dimensional information of the particle at the portion to be examined from a second direction different from said first direction; and means for evaluating three-dimensional information of the particle on the basis of outputs of said first and second detection means.

36. A particle measuring apparatus according to claim 35, wherein said first and second detection means detects the two-dimensional information by substantially performing a light scanning operation on said particle to be examined.

37. A particle measuring apparatus according to claim 35, further comprising means for comparing the outputs of said first and second detection means and for judging the degree of sphericity on the basis of the comparison result.

38. A particle measuring apparatus according to claim 35, wherein said portion to be examined is provided in a flow cell.

39. A particle measuring apparatus according to claim 38, wherein said individual particle is made to flow by a laminar sheath flow principle.

40. A particle measuring apparatus according to claim 35, wherein said particles to be examined are cells.

41. A particle measuring apparatus according to claim 35, wherein said particles to be examined are immunity latex particles.

42. A particle measuring apparatus according to claim 35, wherein said applying means includes a laser light source.

* * * * *

UNITED STATES PATENT AND TRADEMARK OFFICE
CERTIFICATE OF CORRECTION

PATENT NO. : 4,999,513
DATED : March 12, 1991
INVENTOR(S) : YUJI ITO ET AL.

It is certified that error appears in the above-identified patent and that said Letters Patent is hereby corrected as shown below:

On the Title page

Item [57] ABSTRACT

Line 8, "photomets" should read --for photometering--.

SHEET 5 OF 6

FIG. 8, "PROCESSER" should read --PROCESSOR--.

COLUMN 2

Line 21, "direction" should read --directions--.
    Line 44, "diagramatically" should read --diagrammatically--.
    Line 61, Insert as heading --[Embodiment 1]--.

COLUMN 5

Line 66, "O-orderlight" should read --O-order light--.

COLUMN 6

Line 62, "canned" should read --scanned--.

COLUMN 8

Line 41, "photo-detector" should read --photodetector--.
    Line 54, "will not" should read --will not be--.
    Line 65, "excluse" should read --exclusive--.

UNITED STATES PATENT AND TRADEMARK OFFICE
CERTIFICATE OF CORRECTION

PATENT NO. : 4,999,513

DATED : March 12, 1991

INVENTOR(S) : YUJI ITO ET AL.

It is certified that error appears in the above-identified patent and that said Letters Patent is hereby corrected as shown below:

COLUMN 10

Line 59, "comprises" should read --comprise--.

COLUMN 12

Line 11, "comprises" should read --comprise--.
Line 33, "detects" should read --detect--.

Signed and Sealed this

Twenty-third Day of February, 1993

Attest:

STEPHEN G. KUNIN

*Attesting Officer*  *Acting Commissioner of Patents and Trademarks*